(12) United States Patent
Hassler, Jr. et al.

(10) Patent No.: US 7,909,754 B2
(45) Date of Patent: Mar. 22, 2011

(54) NON-INVASIVE MEASUREMENT OF FLUID PRESSURE IN AN ADJUSTABLE GASTRIC BAND

(75) Inventors: William L. Hassler, Jr., Cincinnati, OH (US); Russell L. Holscher, West Chester, OH (US); Lauren S. Perry, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1185 days.

(21) Appl. No.: 11/065,407

(22) Filed: Feb. 24, 2005

(65) Prior Publication Data
US 2006/0189887 A1   Aug. 24, 2006

(51) Int. Cl.
*A61F 2/00* (2006.01)
(52) U.S. Cl. .......................... 600/37; 604/909
(58) Field of Classification Search .............. 600/29–32, 600/37, 593, 561; 604/27, 28; 606/139, 606/141, 157, 201–203, 213, 228, 151; 607/41
See application file for complete search history.

(56) References Cited

U.S. PATENT DOCUMENTS

| | | | |
|---|---|---|---|
| 3,939,823 A | 2/1976 | Kaye et al. | |
| 3,942,535 A | 3/1976 | Schulman | |
| 4,407,296 A | 10/1983 | Anderson | |
| 4,471,635 A | 9/1984 | Winter et al. | |
| 4,571,749 A | 2/1986 | Fischell | |
| 4,738,267 A * | 4/1988 | Lazorthes et al. | 600/561 |
| 5,314,457 A | 5/1994 | Jeutter et al. | |
| 5,522,865 A | 6/1996 | Schulman et al. | |
| 5,531,774 A | 7/1996 | Schulman et al. | |
| 5,540,731 A | 7/1996 | Testerman | |
| 5,562,714 A | 10/1996 | Grevious | |
| 5,603,726 A | 2/1997 | Schulman et al. | |
| 5,713,939 A | 2/1998 | Nedungadi et al. | |
| 5,733,313 A | 3/1998 | Barreras, Sr. et al. | |
| 5,755,748 A | 5/1998 | Borza | |
| 5,776,172 A | 7/1998 | Schulman et al. | |
| 5,807,397 A | 9/1998 | Barreras | |
| 5,876,245 A | 3/1999 | Tomita et al. | |
| 5,938,669 A | 8/1999 | Klaiber et al. | |
| 5,938,691 A | 8/1999 | Schulman et al. | |
| 5,995,874 A | 11/1999 | Borza | |
| 6,058,330 A | 5/2000 | Borza | |
| 6,067,991 A | 5/2000 | Forsell | |
| 6,099,495 A | 8/2000 | Kinghorn et al. | |
| 6,210,347 B1 | 4/2001 | Forsell | |
| 6,285,897 B1 | 9/2001 | Kilcoyne et al. | |
| 6,430,444 B1 | 8/2002 | Borza | |
| 6,442,434 B1 | 8/2002 | Zarinetchi et al. | |

(Continued)

FOREIGN PATENT DOCUMENTS

EP   0930086   7/1999

(Continued)

*Primary Examiner* — Charles A Marmor, II
*Assistant Examiner* — Carrie Dorna

(57) ABSTRACT

A food intake restriction device for forming a restriction in a patient's gastro-intestinal tract and non-invasively communicating pressure data regarding the restriction to an external monitor. The device includes a food intake restriction device implanted substantially about a patient's gastro-intestinal tract to form a restricted opening in the tract. A port is connected to the restriction device. The port contains a working fluid for affecting the size of the restricted opening. A pressure sensing system communicates with the working fluid to measure the pressure of the working fluid. A transmitter communicates the measured fluid pressure to the external monitor.

10 Claims, 10 Drawing Sheets

U.S. PATENT DOCUMENTS

| | | | |
|---|---|---|---|
| 6,450,173 B1 * | 9/2002 | Forsell | 128/899 |
| 6,450,946 B1 | 9/2002 | Forsell | |
| 6,453,907 B1 | 9/2002 | Forsell | |
| 6,454,699 B1 | 9/2002 | Forsell | |
| 6,454,700 B1 | 9/2002 | Forsell | |
| 6,460,543 B1 | 10/2002 | Forsell | |
| 6,461,293 B1 | 10/2002 | Forsell | |
| 6,463,935 B1 | 10/2002 | Forsell | |
| 6,464,628 B1 | 10/2002 | Forsell | |
| 6,470,892 B1 | 10/2002 | Forsell | |
| 6,475,136 B1 | 11/2002 | Forsell | |
| 6,482,145 B1 | 11/2002 | Forsell | |
| 6,689,046 B2 | 2/2004 | Sayet et al. | |
| 2002/0123779 A1 | 9/2002 | Zarinetchi et al. | |
| 2002/0128690 A1 | 9/2002 | Zarinetchi et al. | |
| 2003/0032857 A1 | 2/2003 | Forsell | |
| 2003/0092962 A1 | 5/2003 | Forsell | |
| 2003/0093117 A1 | 5/2003 | Saadat | |
| 2003/0176795 A1 * | 9/2003 | Harris et al. | 600/485 |
| 2004/0082867 A1 * | 4/2004 | Esch et al. | 600/488 |

FOREIGN PATENT DOCUMENTS

WO    WO 2004014245 A1    2/2004

* cited by examiner

NON-INVASIVE MEASUREMENT OF FLUID PRESSURE IN AN ADJUSTABLE GASTRIC BAND

FIELD OF THE INVENTION

The present invention is related generally to a food intake restriction device for the treatment of morbid obesity and, more particularly, to a non-invasive method of determining the fluid pressure within an adjustable gastric band. In particular, the present invention relates to incorporating a pressure sensor within an adjustable gastric band to measure the pressure of a working fluid within the band, and non-invasively communicating the pressure measurement to an external monitor.

BACKGROUND OF THE INVENTION

Obesity is becoming a growing concern, particularly in the United States, as the number of obese people continues to increase, and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. The band is placed so as to form a small gastric pouch above the band and a reduced stoma opening in the stomach. The effect of the band is to reduce the available stomach volume and, thus, the amount of food that can be consumed before becoming "full". Gastric bands have typically comprised a fluid-filled elastomeric balloon with fixed endpoints that encircles the stomach just inferior to the esophago-gastric junction. When fluid is infused into the balloon, the band expands against the stomach, creating a food intake restriction or stoma in the stomach. To decrease this restriction, fluid is removed from the band.

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. An example of such an adjustable gastric band is disclosed in U.S. Pat. No. 6,067,991, entitled "Mechanical Food Intake Restriction Device" which issued on May 30, 2000, and is incorporated herein by reference. It is also known to restrict the available food volume in the stomach cavity by implanting an inflatable elastomeric balloon within the stomach cavity itself. The balloon is filled with a fluid to expand against the stomach walls and, thereby, decrease the available food volume within the stomach.

With each of the above-described food restriction devices, safe, effective treatment requires that the device be regularly monitored and adjusted to vary the degree of restriction applied to the stomach. With banding devices, the gastric pouch above the band will substantially increase in size following the initial implantation. Accordingly, the stoma opening in the stomach must initially be made large enough to enable the patient to receive adequate nutrition while the stomach adapts to the banding device. As the gastric pouch increases in size, the band may be adjusted to vary the stoma size. In addition, it is desirable to vary the stoma size in order to accommodate changes in the patient's body or treatment regime, or in a more urgent case, to relieve an obstruction or severe esophageal dilatation. Traditionally, adjusting a hydraulic gastric band required a scheduled clinician visit during which a hypodermic needle and syringe were used to permeate the patient's skin and add or remove fluid from the balloon. More recently, implantable pumps have been developed which enable non-invasive adjustments of the band. An external programmer communicates with the implanted pump using telemetry to control the pump. During a scheduled visit, a physician places a hand-held portion of the programmer near the gastric implant and transmits power and command signals to the implant. The implant in turn adjusts the fluid levels in the band and transmits a response command to the programmer.

During these gastric band adjustments, it has been difficult to determine how the adjustment is proceeding, and whether the adjustment will have the intended effect. In an attempt to determine the efficacy of an adjustment, some physicians have utilized fluoroscopy with a Barium swallow as the adjustment is being performed. However, fluoroscopy is both expensive and undesirable due to the radiation doses incurred by both the physician and patient. Other physicians have instructed the patient to drink a glass of water during or after the adjustment to determine whether the water can pass through the adjusted stoma. This method, however, only assures that the patient is not obstructing, and does not provide any information about the efficacy of the adjustment. Oftentimes, a physician may simply adopt a "try as you go" method based upon their prior experience, and the results of an adjustment may not be discovered until hours or days later, when the patient experiences a complete obstruction of the stomach cavity, or the band induces erosion of the stomach tissue.

Accordingly, it is desirable to provide an effective method for evaluating an adjustment of a food intake restriction device during or immediately after an adjustment. In particular, it is desirable to provide a gastric restriction device that includes a pressure measuring system for measuring the pressure within the restriction device and, accordingly, the stoma size. In addition, it is desirable to provide a non-invasive method for measuring fluid pressure during an adjustment and communicating the pressure measurement to an external monitor.

SUMMARY OF THE INVENTION

The present invention provides a method for non-invasively measuring the pressure of a fluid inside an implanted food intake restriction device. The method includes implanting a food intake restriction device in the gastro-intestinal tract of a patient and using a working fluid in the restriction device to form a restricted opening in the gastro-intestinal tract. The pressure in the restricted opening is determined by measuring the pressure of the working fluid with a pressure sensor in communication with the working fluid. An external monitor is placed adjacent to the pressure sensor. A measured pressure signal is transmitted from the pressure sensor to the external monitor and displayed on an external display.

In another embodiment, the present invention provides a food intake restriction system for forming a restriction in a patient's gastro-intestinal tract and non-invasively communicating pressure data regarding the restriction to an external monitor. The system includes a food intake restriction device implanted to form a restriction in the patient's gastro-intestinal tract. A port is connected to the restriction device. The port contains a working fluid for affecting the size of the restricted opening. A pressure sensing system communicates with the working fluid to measure the pressure of the working fluid. A transmitter communicates the measured fluid pressure to the external monitor.

In yet another embodiment, the present invention provides an implanted bariatric treatment device for forming a food intake restriction in a patient's stomach and communicating the pressure of the restriction to an external monitor. The device includes a restriction member implanted in contact with the patient's stomach. The restriction member has a variable fluid volume to create a food intake restriction in the stomach. A control is operatively connected to the restriction member to vary the volume of the restriction member. A pressure sensing system measures the fluid pressure within the restriction member, and non-invasively communicates the measured pressure to the external monitor. The fluid pressure measurement is proportional to the degree of restriction formed in the stomach.

DETAILED DESCRIPTION OF THE INVENTION

Figure 1:
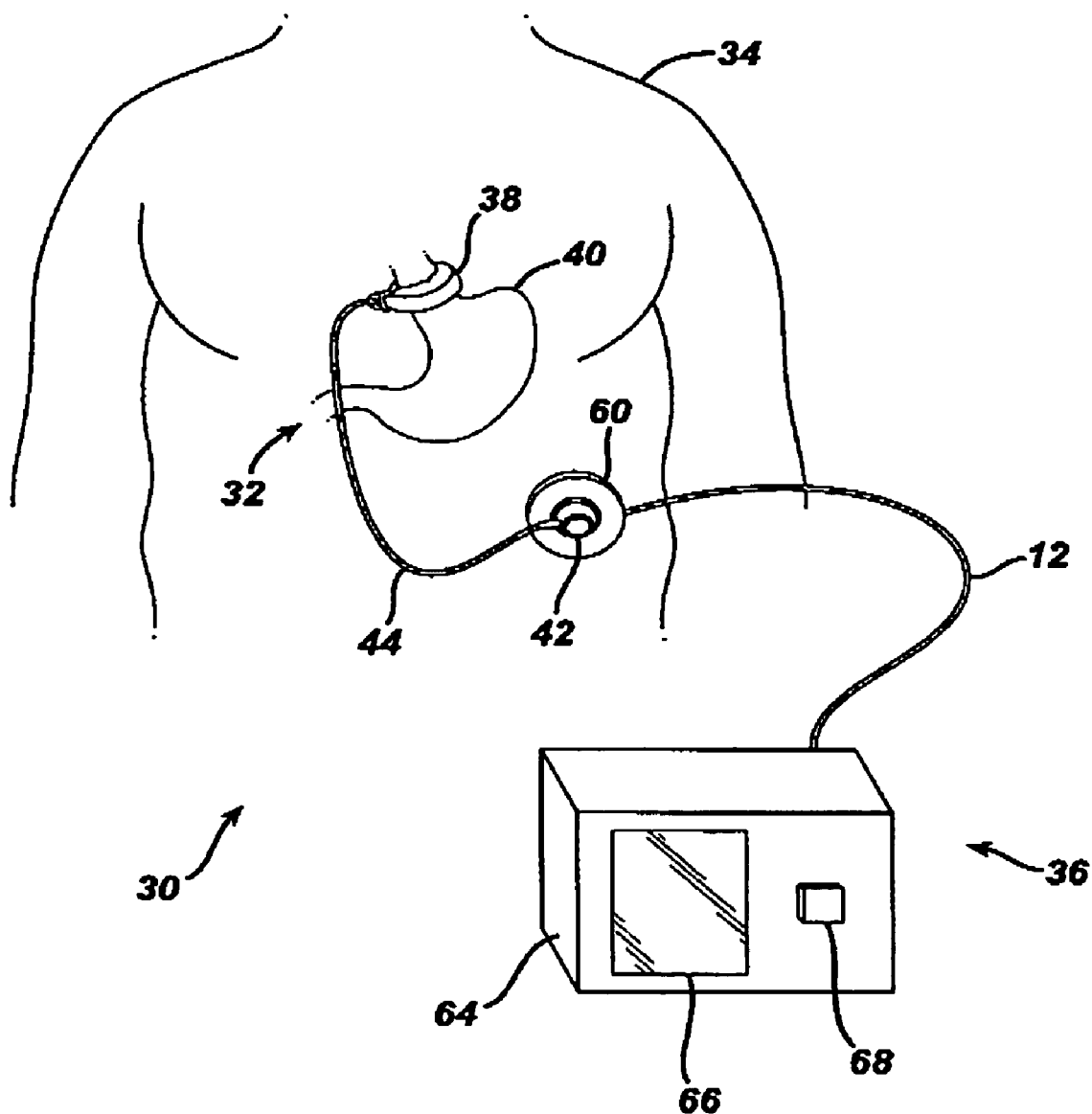
FIG. 1 is a schematic illustration of a food intake restriction device of the present invention.

Referring now to the drawings in detail, wherein like numerals indicate the same elements throughout the views, FIG. 1 illustrates a food intake restriction system 30. System 30 comprises a first portion, identified generally as 32, implanted inside of a patient 34, and a second portion, identified generally as 36, located external to the patient. Implanted portion 32 comprises an adjustable gastric band 38 positioned on the upper portion of the patient's stomach 40. Adjustable band 38 may include a cavity made of silicone rubber, or another type of biocompatible material, that inflates inwardly against stomach 40 when filled with a fluid. Alternatively, band 38 may comprise a mechanically adjustable device having a fluid cavity that experiences pressure changes with band adjustments, or a combination hydraulic/mechanical adjustable band. An injection port 42, which will be described in greater detail below, is implanted in a body region accessible for needle injections and/or telemetry communication signals. In the embodiment shown, injection port 42 fluidly communicates with adjustable band 38 via a catheter 44. A surgeon may position and permanently implant injection port 42 inside the body of the patient in order to perform adjustments of the food intake restriction or stoma. Those skilled in the art will recognize that the surgical methods for placing gastric band systems such as implantable portion 32 have evolved greatly during recent years so that the patient may derive optimal therapeutic effect with minimal complications. The surgeon, for example, typically implants injection port 42 in the lateral, subcostal region of the patient's abdomen under the skin and layers of fatty tissue. The surgeon may also implant injection port 42 on the sternum of the patient.

Figure 2:
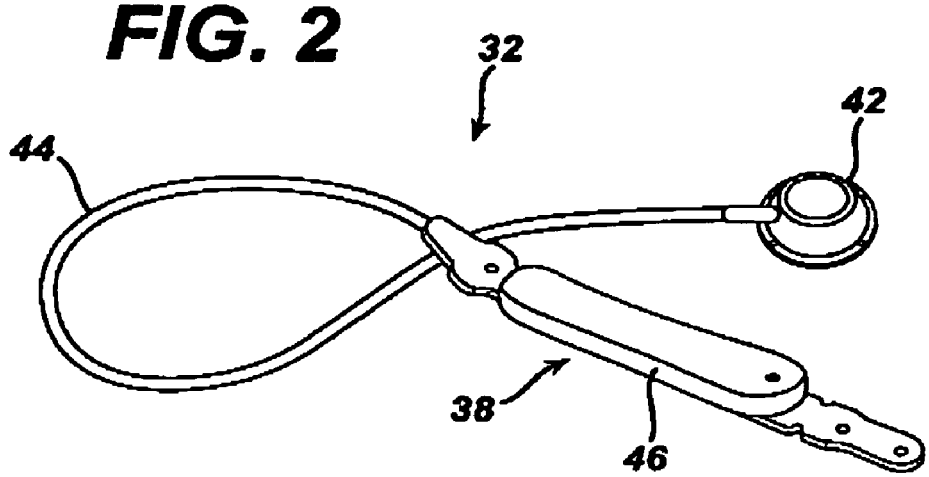
FIG. 2 is a more detailed perspective view of an exemplary implantable portion for the food intake restriction device of FIG. 1.

FIG. 2 illustrates an exemplary adjustable gastric band in greater detail. In this embodiment, band 38 includes a variable volume cavity 46 that expands or contracts against the outer wall of the stomach to form an adjustable stoma for controllably restricting food intake into the stomach. A physician may decrease the size of the stoma opening by adding fluid to variable volume cavity 46 or, alternatively, may increase the stoma size by withdrawing fluid from the cavity. Fluid may be added or withdrawn by inserting a needle into injection port 42. Alternatively, fluid may be transferred in a non-invasive manner between band 38 and injection port 42 using telemetry command signals. The fluid may be, but is not restricted to, a 0.9 percent saline solution.

Figure 3:
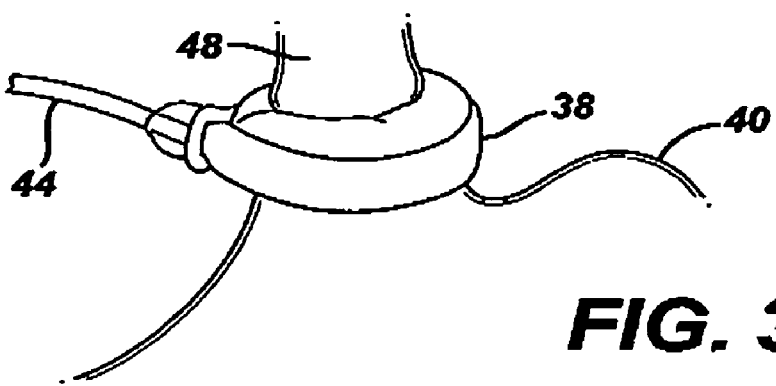
FIG. 3 is a perspective view of the adjustable gastric band of FIG. 2, showing the band positioned around the gastro-esophageal junction of a patient.
Figure 4:
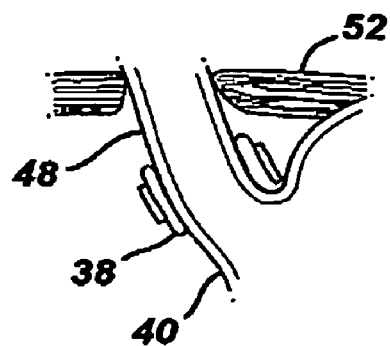
FIG. 4 is a sectional view of the adjustable gastric band of FIG. 2, shown in a deflated configuration.
Figure 5:
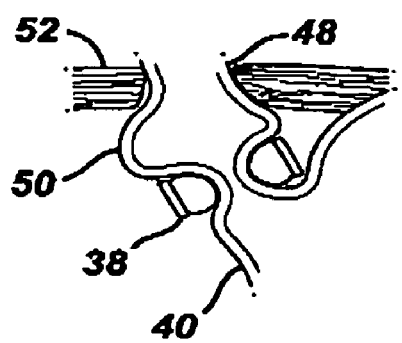
FIG. 5 is a sectional view of the adjustable gastric band of FIG. 2, shown in an inflated configuration to create a food intake restriction.

FIG. 3 shows the adjustable gastric band 38 of FIG. 2 applied about the gastro-esophageal junction of a patient. As shown in FIG. 3, band 38 at least substantially encloses the upper portion of stomach 40 near the junction with esophagus 48. FIG. 4 is a sectional view of band 38, showing the band in a deflated configuration. In this view, band 38 contains little to no fluid, thereby maximizing the size of the stoma opening into stomach 40. FIG. 5 is a cross-sectional view of band 38 and stomach 40, similar to FIG. 4, showing band 38 in an inflated, fluid-filled configuration. In this view, the pressure of band 38 against stomach 40 is increased due to the fluid within the band, thereby decreasing the stoma opening to create a food intake restriction. FIG. 5 also schematically illustrates the dilation of esophagus 48 above band 38 to form an upper pouch 50 beneath the diaphragm muscle 52 of the patient.

Returning now to FIG. 1, external portion 36 of food restriction system 30 comprises a pressure-reading device 60 electrically connected (in this embodiment via an electrical cable assembly 62) to a control box 64. Control box 64 includes a display 66, one or more control switches 68, and an external control module, which will be explained in further detail below. Control box 64 may be configured for use, for example, in a physician's office or examination room. Some ways to mount control box 64 include placement upon a desktop, attachment to an examination table, or hanging on a portable stand. Control box 64 may also be configured for carrying in the physician's lab coat pocket, holding by hand, or placing upon the examination table or the reclining patient. Electrical cable assembly 62 may be detachably connected to control box 64 or pressure-reading device 60 to facilitate cleaning, maintenance, usage, and storage of external portion 36 of system 30. Pressure-reading device 60 non-invasively measures the pressure of the fluid within implanted portion 32 even when injection port 42 is implanted beneath thick (at least over 10 centimeters) subcutaneous fat tissue. The physician may hold pressure-reading device 60 against the patient's skin near the location of injection port 42 in the patient and observe the pressure reading on display 66 of control box 64. Pressure-reading device 60 may also be removably attached to the patient, such as during a prolonged examination, using straps, adhesives, and other well-known methods. Pressure-reading device 60 operates through conventional cloth or paper surgical drapes, and may also include a disposal cover (not shown) that may be replaced for each patient.

Figure 6:
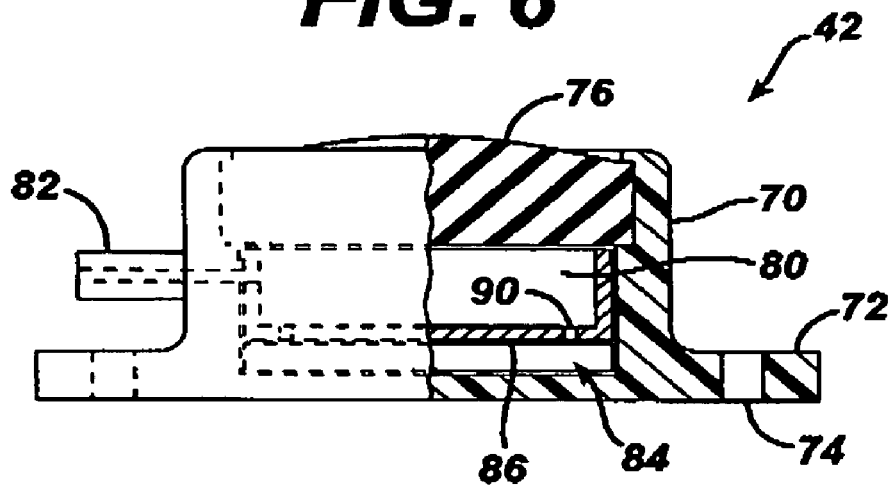
FIG. 6 is a side, partially sectioned view of the injection port shown in FIG. 2.

Turning now to FIG. 6, which depicts a side, partially sectioned view of injection port 42 containing a pressure sensing system for non-invasively measuring the fluid pressure within implanted portion 32. As shown in FIG. 6, injection port 42 comprises a rigid housing 70 having an annular flange 72 containing a plurality of attachment holes 74 for fastening the injection port to tissue in a patient. A surgeon may attach injection port 42 to the tissue, such as the fascia covering an abdominal muscle, using any one of numerous surgical fasteners including suture filaments, staples, and clips. Injection port 42 further comprises a septum 76 typically made of a silicone rubber and compressively retained in housing 70. Septum 76 is penetrable by a Huber needle, or a similar type of injection instrument, for adding or withdrawing fluid from the port. Septum 76 self-seals upon withdrawal of the syringe needle to maintain the volume of fluid inside of injection port 42. Injection port 42 further comprises a reservoir 80 for retaining a working fluid and a catheter connector 82. Connector 82 attaches to catheter 44, shown in FIG. 2, to form a closed hydraulic circuit between reservoir 80 inside of injection port 42 and cavity 46 within adjustable band 38. Fluid from reservoir 80 may be used to expand the volume of band cavity 46. Alternatively, fluid may be removed from cavity 46 and retained in reservoir 80 in order to temporarily decrease the volume of cavity 46. Housing 70 and connector 82 may be integrally molded from a biocompatible polymer or constructed from a metal such as titanium or stainless steel.

A pressure sensing system is provided in injection port 42 to measure the fluid pressure within the closed hydraulic circuit of implanted portion 32. The pressure within the circuit corresponds to the amount of restriction applied by adjustable band 38 to the patient's stomach. Accordingly, measuring the fluid pressure enables a physician to evaluate the restriction created by a band adjustment. Fluid pressure may be measured before, during and/or after an adjustment to verify that the band is properly adjusted. In the embodiment shown in FIG. 6, the pressure sensing system comprises a sensor 84 positioned at the bottom of fluid reservoir 80 within housing 70. A retaining cover 86 extends above pressure sensor 84 to substantially separate the sensor surface from reservoir 80, and protect the sensor from needle penetration. Retaining cover 86 may be made of a ceramic material such as, for example, alumina, which resists needle penetration yet does not interfere with electronic communications between pressure sensor 84 and pressure-reading device 60. Retaining cover 86 includes a vent 90 that allows fluid inside of reservoir 80 to flow to and impact upon the surface of pressure sensor 84.

Figure 7:
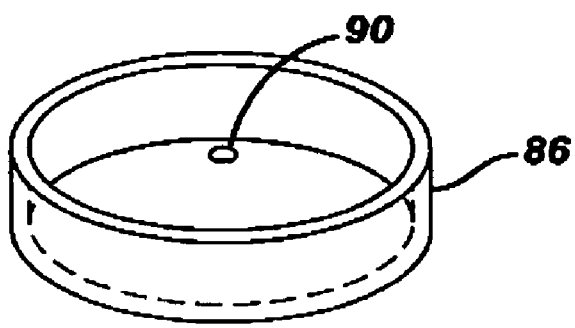
FIG. 7 is an isometric view of the retaining cover shown in FIG. 6.
Figure 8:
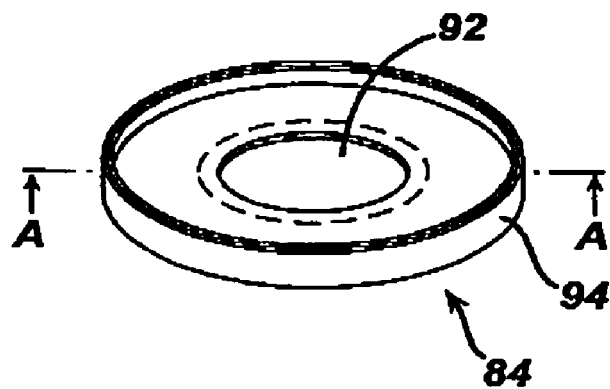
FIG. 8 is an isometric view of the pressure sensor shown in FIG. 6.

FIG. 7 is an isometric view of retaining cover 86 illustrating vent 90 in the bottom surface of the cover. FIG. 8 is an isometric view of the exterior of pressure sensor 84. As shown in FIG. 8, the exterior of pressure sensor 84 includes a strain element having a deformable surface. In the embodiment shown, the strain element is a diaphragm 92. Diaphragm 92 may be formed by thinning out a section of a wall in titanium reservoir 80. Diaphragm 92 may be made of titanium or another similar material, and have a thickness between 0.001" and 0.002". While the embodiments show a diaphragm as the strain element, the present invention may also be constructed and practiced using other strain elements to convert fluid pressure to a mechanical displacement. Examples of other suitable strain elements include, but are not limited to, Bourdon tubes and bellows assemblies. Pressure sensor 84 is hermetically sealed within a housing 94 to prevent fluid infiltrating and effecting the operation of the sensor. Housing 94 is sealed to port housing 70 to prevent the loss of fluid from the injection port 42. Diaphragm 92 is hermetically sealed to sensor housing 94 to prevent fluid from passing around the edges of the diaphragm and into the internal components of the sensing system. As fluid flows through vent 90 in reservoir 80, the fluid impacts upon the surface of diaphragm 92. The fluid flow through vent 90 enables diaphragm 92 to respond to fluid pressure changes within the hydraulic circuit and convert the pressure changes into a mechanical displacement.

Figure 9:
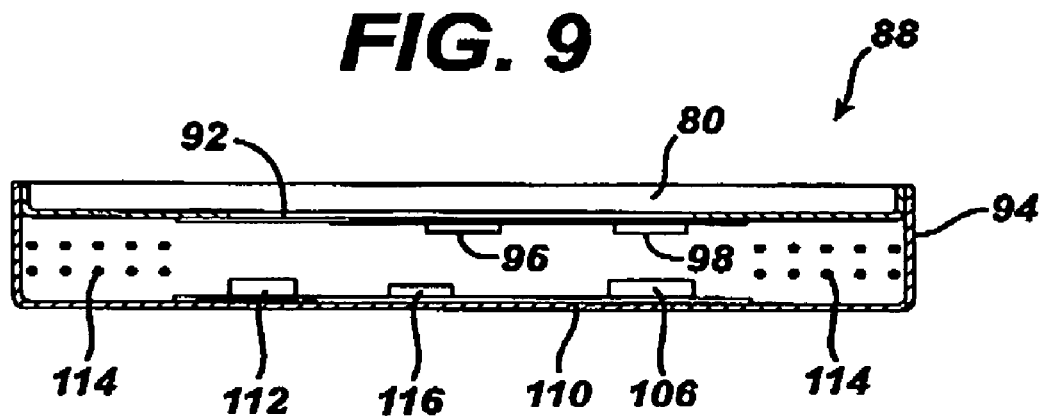
FIG. 9 is a side sectional view illustrating a first embodiment for the pressure sensing system of the present invention.

FIG. 9 is a side sectional view of pressure sensor 84, taken along line A-A of FIG. 8, illustrating a first embodiment 88 for measuring fluid pressure. In the embodiment shown in FIG. 9, the mechanical displacement of diaphragm 92 is converted to an electrical signal by a pair of variable resistance, silicon strain gauges 96, 98. Strain gauges 96, 98 are attached to diaphragm 92 on the side opposite the working fluid in reservoir 80. Strain gauge 96 is attached to a center portion of diaphragm 92 to measure the displacement of the diaphragm. The second, matched strain gauge 98 is attached near the outer edge of diaphragm 92. Strain gauges 96, 98 may be attached to diaphragm 92 by adhesives, or may be diffused into the diaphragm structure. As the fluid pressure within band 38 changes, the surface of diaphragm 92 deforms up or down within the surface of housing 94. This deformation of diaphragm 92 produces a resistance change in the center strain gauge 96.

Figure 10:
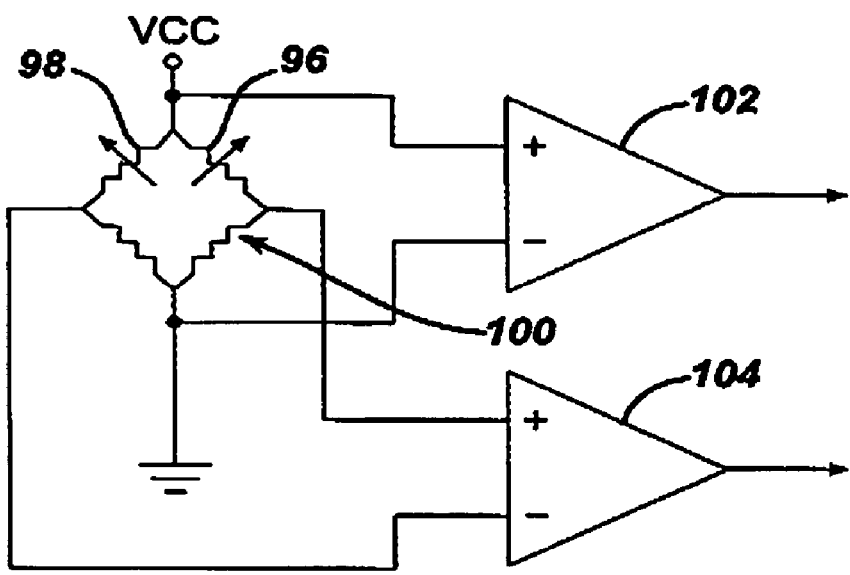
FIG. 10 is a simplified schematic of the variable resistance circuit of the first embodiment.

As shown in FIG. 10, strain gauges 96, 98 form the top two resistance elements of a half-compensated, Wheatstone bridge circuit 100. As strain gauge 96 reacts to the mechanical deformations of diaphragm 92, the changing resistance of the gauge changes the potential across the top portion of the bridge circuit. Strain gauge 98 is matched to strain gauge 96 and athermalizes the Wheatstone bridge circuit. Differential amplifiers 102, 104 are connected to bridge circuit 100 to measure the change in potential within the bridge circuit due to the variable resistance strain gauges. In particular, differential amplifier 102 measures the voltage across the entire bridge circuit, while differential amplifier 104 measures the differential voltage across the strain gauge half of bridge circuit 100. The greater the differential between the strain gauge voltages, for a fixed voltage across the bridge, the greater the pressure difference. If desired, a fully compensated Wheatstone bridge circuit could also be used to increase the sensitivity and accuracy of the pressure sensing system. In a fully compensated bridge circuit, four strain gauges are attached to the surface of diaphragm 92, rather than only two strain gauges as shown in FIG. 9.

The output signals from differential amplifiers 102, 104 are applied to a microcontroller 106. Microcontroller 106 is integrated into a circuit board 110 within housing 94. A temperature sensor 112 measures the temperature within the implanted port and inputs a temperature signal to microcontroller 106. Microcontroller 106 uses the temperature signal from sensor 112 to compensate for variations in body temperature and residual temperature errors not accounted for by strain gauge 98. Compensating the pressure measurement signal for variations in body temperature increases the accuracy of the pressure sensing system. Additionally, a TET/telemetry coil 114 is located within housing 94. Coil 114 is connected to a capacitor 116 to form a tuned tank circuit for receiving power from external portion 36, and transmitting the pressure measurement to pressure reading device 60.

Figure 11:
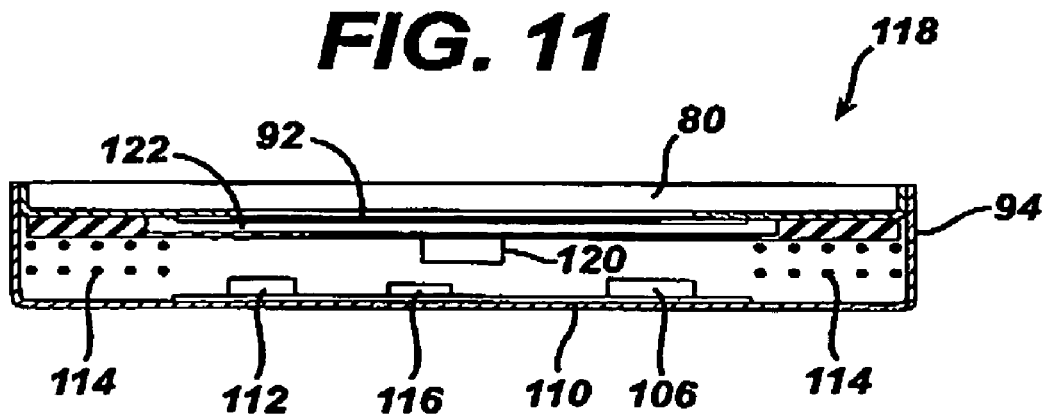
FIG. 11 is a side, sectional view of a second embodiment for the pressure sensing system of the invention.

FIG. 11 is a side, sectional view similar to FIG. 9, showing a second embodiment 118 for the pressure sensing system of the present invention. In second embodiment 118, a MEMS sensor 120 is provided within housing 94 to measure the mechanical deformation of diaphragm 92 and produce an electrical signal proportional to the pressure within adjustable band 38. A sealed, silicone oil chamber 122 is provided between diaphragm 92 and MEMS sensor 120. Oil chamber 122 protects MEMS sensor 120 and transfers the mechanical displacements of diaphragm 92 to the sensor. MEMS sensor 120 outputs an electrical signal to microcontroller 106 indicative of the fluid pressure in reservoir 80. Microcontroller 106 inputs the signal from the MEMS sensor 120 and a temperature signal from temperature sensor 112, and calculates the pressure measurement. The pressure measurement is transmitted to pressure reading device 60 in external portion 36 using telemetry signals, as will be described in more detail below.

Figure 12:
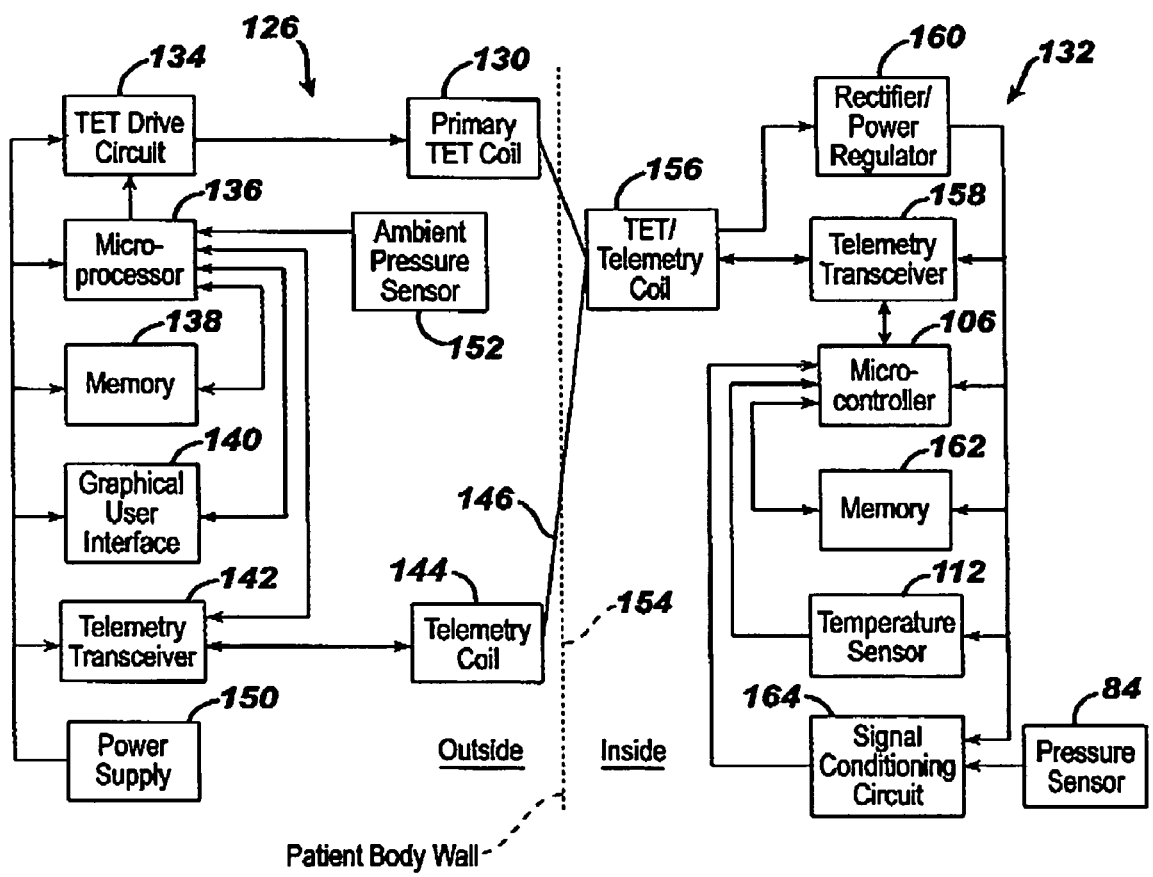
FIG. 12 is a block diagram representing a pressure measurement system associated with the first and second embodiments of the invention.

FIG. 12 is a block diagram of a pressure measurement system for first and second embodiments 88, 118 of the invention. As shown in FIG. 12, an external control module 126 of the system includes a primary TET coil 130 for transmitting a power signal to the internal control module, indicated generally as 132. Primary TET coil 130 is located in pressure reading device 60 shown in FIG. 1. A TET drive circuit 134 controls the application of a power signal to primary TET coil 130. TET drive circuit 134 is controlled by a microprocessor 136 having an associated memory 138. A graphical user interface 140 is connected to microprocessor 136 for controlling the data shown on display 66. External control module 126 also includes a primary telemetry transceiver 142 for transmitting interrogation commands to and receiving response data, including fluid pressure readings, from implant control module 132. Primary transceiver 142 is electrically connected to microprocessor 136 for inputting and receiving command and data signals. Primary transceiver 142 resonates at a selected RF communication frequency to generate a downlink alternating magnetic field 146 that transmits command data to implant control module 132. A power supply 150 supplies energy to external control module 126 in order to power system 30. An ambient pressure sensor 152 is connected to microprocessor 136. Microprocessor 136 uses the signal from ambient pressure sensor 152 to adjust the pressure reading for variations in atmospheric pressure due to, for example, variations in barometric conditions or altitude, in order to increase the accuracy of the pressure measurement.

FIG. 12 also illustrates internal control module 132 implanted beneath the patient's skin 154. Internal control module 132 is located within housing 94 of injection port 42. As shown in FIG. 12, a secondary TET/telemetry coil 156 in internal control module 132 receives power and communication signals from external control module 126. Coil 156 forms a tuned tank circuit that is inductively coupled with either primary TET coil 130 to power the implant, or primary telemetry coil 144 to receive and transmit data. A telemetry transceiver 158 controls data exchange with coil 156. Additionally, internal control module 132 includes a rectifier/power regulator 160, microcontroller 106 described above, a memory 162 associated with the microcontroller, temperature sensor 112, pressure sensor 84 and a signal conditioning circuit 164 for amplifying the signal from the pressure sensor. Internal control module 132 transmits the temperature adjusted pressure measurement from pressure sensor 84 to external control module 126. In external module 126, the received pressure measurement signal is adjusted for changes in ambient pressure and shown on display 66.

Figure 13:
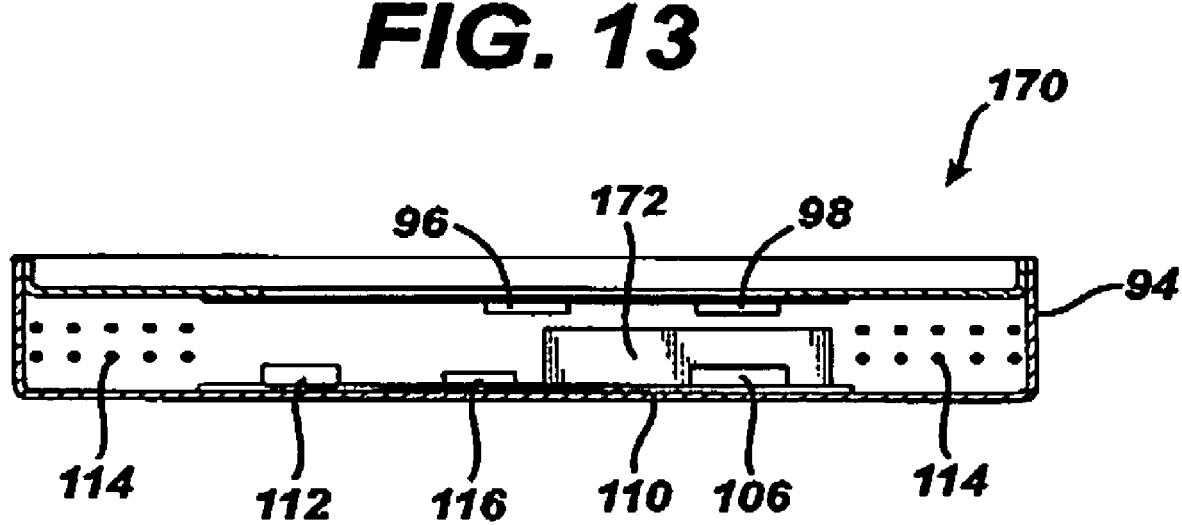
FIG. 13 is a side, sectional view of a third embodiment for the pressure sensing system of the invention.

FIG. 13 is a side, sectional view showing a third embodiment 170 for measuring fluid pressure in accordance with the invention. In the third embodiment 170, internal control module 132 is powered by an internal power supply such as, for example, a battery 172. Battery 172 replaces primary and secondary TET coils 130, 156 for powering microcontroller 106 and the other internal components. In this embodiment, the pressure sensing system includes a pair of strain gauges 96, 98 as in first embodiment 88, for measuring the mechanical deformations of diaphragm 92 corresponding to pressure changes in band 38. Strain gauges 96, 98 are incorporated into a balanced, thermally compensated bridge circuit for measuring pressure differentials within the closed fluid circuit of the implant.

Figure 14:
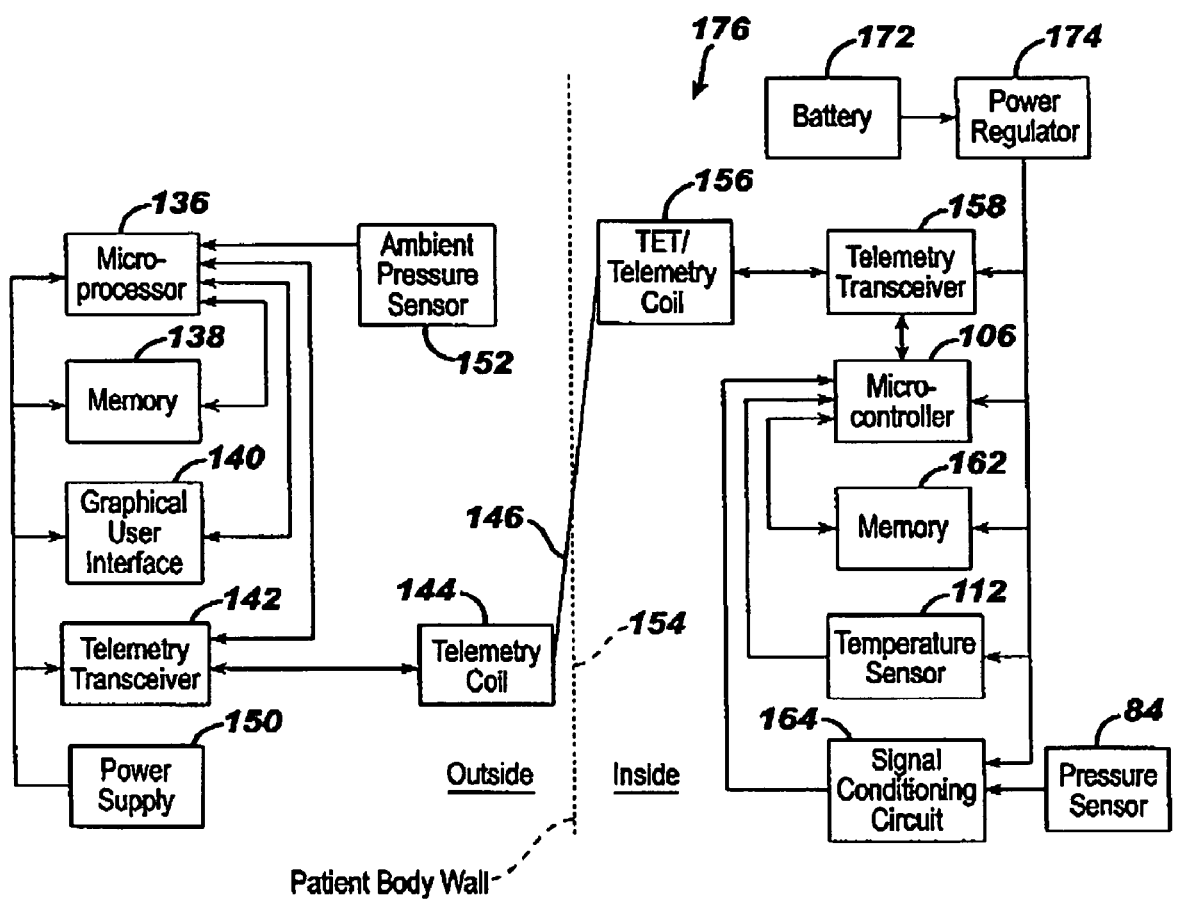
FIG. 14 is a block diagram representing a pressure measurement system associated with the third embodiment of the invention.

FIG. 14 is a block diagram of the pressure measurement system of the invention in accordance with the third embodiment 170 shown in FIG. 13. In embodiment 170, an internal power supply is used to power internal control module 176 rather than a TET power system as in the first embodiment. The power source for implanted portion 32 is battery 172 rather than the TET primary coil 130 and secondary coil 156 shown in FIG. 12. In the embodiment shown in FIG. 14, secondary, implanted coil 156 is used solely for data communication between the internal and external control modules. A power regulator 174 is provided to control power from battery 172 in order to conserve and extend the life of the battery.

Figure 15:
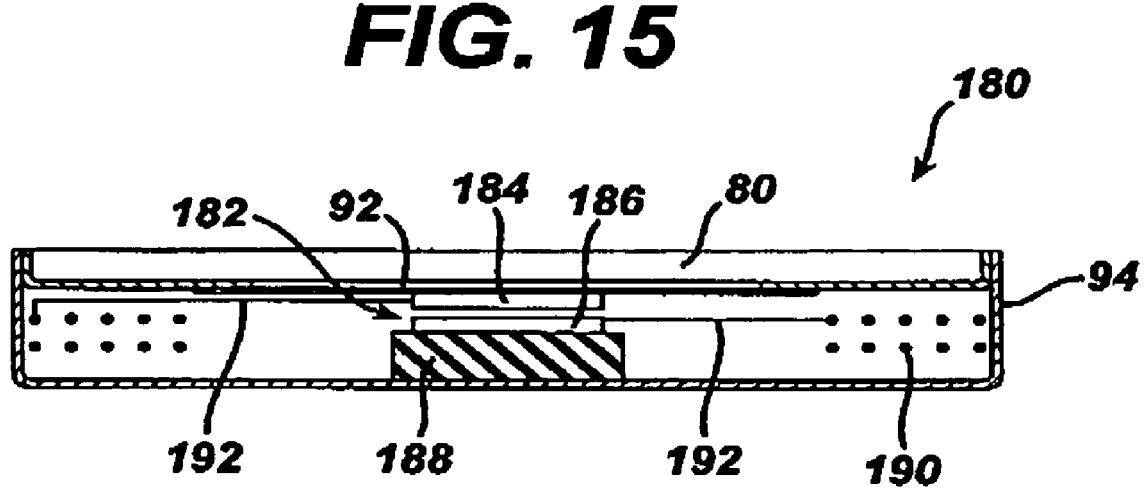
FIG. 15 is a side, sectional view of a fourth embodiment for the pressure sensing system of the invention.

FIG. 15 illustrates a fourth embodiment 180 for measuring fluid pressure within adjustable band 38, in which a passive system is utilized for measuring pressure changes within the working fluid. In this fourth embodiment 180, a variable capacitance 182 is attached to diaphragm 92 in order to measure the mechanical deformations of the diaphragm. Variable capacitance 182 includes a first plate 184 attached near the center of diaphragm 92 on the side opposite fluid reservoir 80. A second capacitor plate 186 is fixed in position within housing 94 by a capacitor mount 188. Each of the capacitor plates 184, 186 is connected to an inductance coil 190, as shown by lines 192, to form a resonant circuit. When the fluid pressure within reservoir 80 increases or decreases due to, for instance, changes in the peristaltic pressure against band 38, the position of capacitor plate 184 varies with the deformation of diaphragm 92. As fluid pressure increases, diaphragm 92 pushes first capacitor plate 184 closer to second capacitor plate 186, thereby increasing the capacitance and decreasing the resonant frequency. Likewise, when the hydraulic pressure decreases within the closed implant circuit, first capacitor plate 184 moves with diaphragm 92 in a direction away from second plate 186, thereby decreasing the capacitance within the resonant circuit and increasing the resonant frequency.

Figure 16:
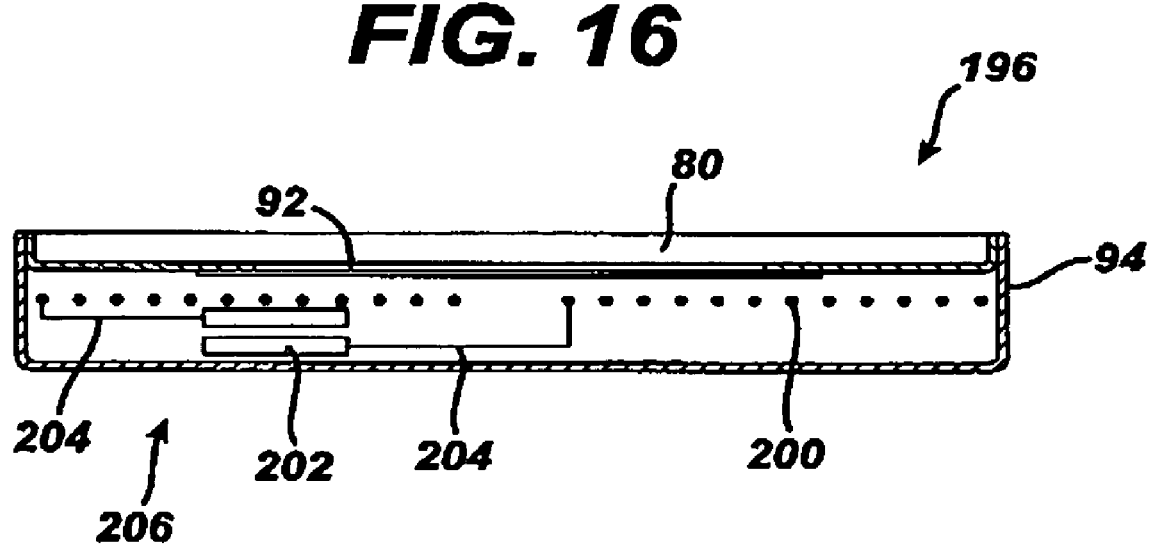
FIG. 16 is a side, sectional view of a fifth embodiment of the pressure sensing system of the invention.

FIG. 16 shows a fifth embodiment 196 for measuring fluid pressure in accordance with the present invention. Fifth embodiment 196 is an alternative embodiment for a passive pressure sensing system, in which a variable inductance coil 200 converts the mechanical deformations of diaphragm 92 into a pressure measurement signal. As shown in FIG. 16, inductance coil 200 is a flat coil spaced beneath diaphragm 92. A fixed capacitance 202 is connected to inductance coil 200, as shown by lines 204, to form an LC resonant circuit 206. As diaphragm 92 deforms up and down in response to pressure variations in the working fluid, the inductance of coil 200 varies. As the fluid pressure increases, diaphragm 92 deforms in the direction of coil 200, thereby decreasing the inductance of coil 200 due to eddy current coupling between the metal diaphragm and coil. Conversely, when fluid pressure decreases, diaphragm 92 deforms away from coil 200, thereby decreasing the eddy current coupling and increasing the inductance of the coil. Accordingly, the inductance of coil 200 is inversely proportional to the pressure of the working fluid. As the inductance of coil 200 changes, the resonant frequency of the LC circuit 206 changes.

Figure 17:
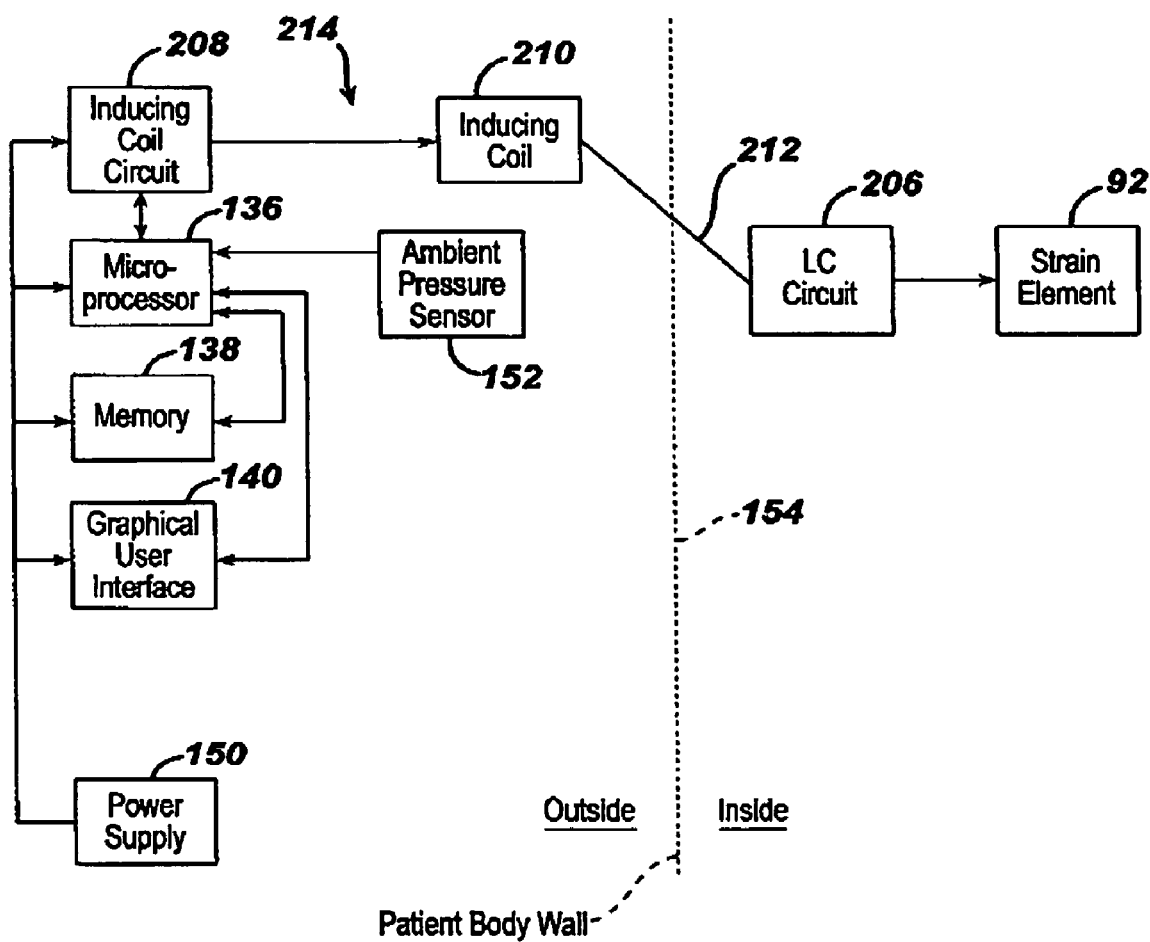
FIG. 17 is a block diagram of a pressure measurement system associated with the fourth and fifth embodiments of the invention.

FIG. 17 is a block diagram of a pressure measurement system for the fourth and fifth embodiments 180, 196 of the invention. In this system, microprocessor 136 controls an inducing coil circuit 208 and inducing coil 210. Microprocessor 136 varies the frequency of inducing coil 210 to magnetically couple the coil with LC circuit 206 in implanted portion 32, as indicated by line 212. The frequency at which the internal and external coils couple will vary with the resonant frequency of the implanted LC circuit 206. The resonant frequency of the implanted LC circuit will vary with the fluid pressure within band 38. The variation in resonant frequency is measured by microprocessor 136 through inducing coil circuit 208. Once detected, the resonant frequency may be compared to known pressures at designated frequencies to determine the fluid pressure within band 38. A graphical user interface 140 in external module 214 displays the measured fluid pressure on display 66.

Figure 18:
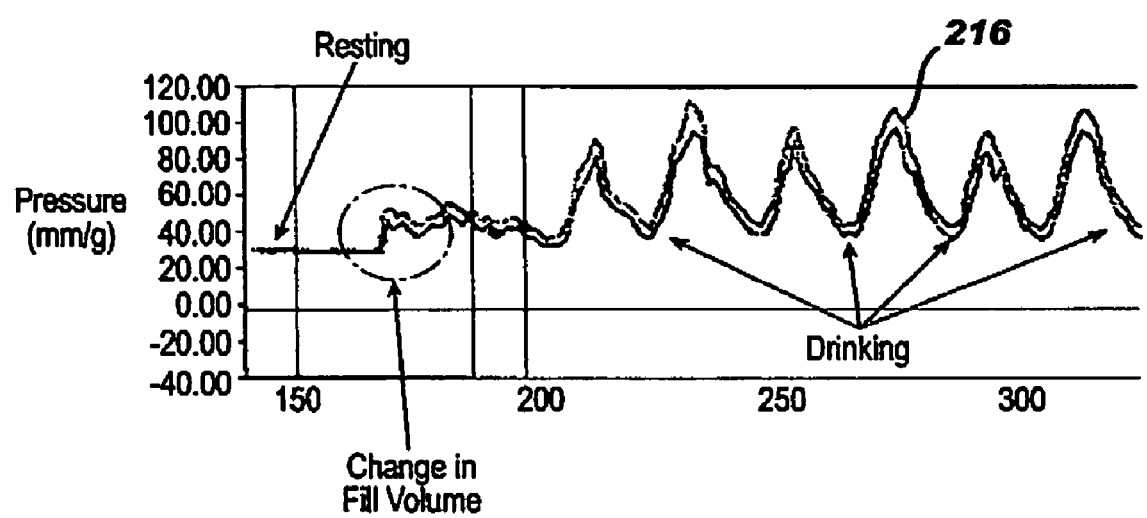
FIG. 18 is a graph indicating a pressure signal from the pressure sensing system, such as may appear on the external monitor display during interrogation by a user.

FIG. 18 is a graphical representation of a pressure signal 216 from the pressure sensing system of the invention, such as may appear on display 66 during interrogation by a user. In the example shown in FIG. 18, the fluid pressure is initially measured by pressure reading device 60 while the patient is stable, resulting in a steady pressure reading as shown. Next, an adjustment is applied to band 38 to decrease the stoma size. During the band adjustment, the pressure sensing system continues to measure the fluid pressure and transmit the pressure readings through the patient's skin to device 60. As seen in the graph of FIG. 18, the pressure reading rises slightly following the band adjustment. In the example shown, the patient is then asked to drink a liquid to check the accuracy of the adjustment. As the patient drinks, the pressure sensing system continues to measure the pressure spikes due to the peristaltic pressure of swallowing the liquid, and transmit the pressure readings to external module 36 for display. By measuring and visually depicting the loading of the restriction device against the peristaltic motion of the stomach both during and after an adjustment, the present invention provides the physician with an accurate, real-time visualization of the patient's response to the adjustment. This instantaneous, active display of recorded pressure data enables the physician to perform more accurate band adjustments. The data may be displayed over time to provide a pressure verses time history.

In addition to use during adjustments, the pressure sensing system of the invention may also be used to measure pressure variations in the restriction device at various intervals during treatment. Periodic pressure readings enable the pressure sensing system to function as a diagnostic tool, to ensure that the food intake restriction device is operating effectively. In particular, the pressure sensing system may be utilized to detect a no pressure condition within the band, indicating a fluid leakage. Alternatively, the system may be used to detect excessive pressure spikes within the band, indicating a kink in catheter 44 or a blockage within the stoma.

The pressure sensing system of the invention also enables a patient to track their own treatment, utilizing an external monitor, such as external device 36, at home. Using the external device, the patient may routinely download pressure readings to their physician's office, thereby reducing the number of office visits required to monitor the patient's treatment. Additionally, the patient could perform pressure readings at home and notify their physician when the band pressure drops below a specified baseline, indicating the need for an adjustment of the device. The pressure sensing system of the invention thus has benefits as both a diagnostic and a monitoring tool during patient treatment with a bariatric device.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the device and method of the present invention has been illustrated in relation to providing the pressure sensor within the injection port. Alternatively, the sensor could be positioned within a fluid filled portion of the band in order to measure pressure changes within the band. Additionally, the pressure sensor could be associated with an elastomeric balloon implanted within the stomach cavity to measure fluid pressure within the balloon. The structure of each element associated with the present invention can be alternatively described as a means for providing the function performed by the element. It will be understood that the foregoing description is provided by way of example, and that other modifications may occur to those skilled in the art without departing from the scope and spirit of the appended Claims.

What is claimed:

1. A food intake restriction system for forming a restriction in a patient's gastro-intestinal tract and non-invasively communicating pressure data regarding the restriction to an external monitor, the system comprising:
    a food intake restriction device adapted to be implanted to form a restriction in a patient's gastro-intestinal tract;
    an implanted port connected to the restriction device, said implanted port comprising a self-sealing septum which is penetrable by an external needle and will seal upon withdraw of said needle, the port and the restriction device containing a working fluid for affecting the size of the restriction in the gastro-intestinal tract; and
    a pressure sensing system in communication with the working fluid and disposed within the implanted port for making periodic measurements the pressure of the working fluid in the implanted port and restriction device at various intervals and transmitting pressure measurement data to the external monitor.

2. The food intake restriction system of claim 1, wherein the pressure of the working fluid is proportional to the degree of restriction formed in the gastro-intestinal tract.

3. The food intake restriction system of claim 2, wherein the pressure sensing system includes a mechanically deformable surface in contact with the working fluid, and wherein the surface deforms in proportion to the pressure of the working fluid.

4. The food intake restriction system of claim 3, wherein the mechanical deformations of the surface are converted into an electrical signal indicative of the pressure within the working fluid.

5. The food intake restriction system of claim 4, wherein the pressure sensing system comprises two or more variable resistance elements attached to the deformable surface, the resistance of the elements varying in response to the mechanical deformations of the surface; and wherein the resistance elements are connected in an electrical circuit, the output of the circuit providing a measurement of the working fluid pressure.

6. The food intake restriction system of claim 5, further comprising a tuned tank circuit in the port for non-invasively transmitting the pressure measurement data from the variable resistance circuit to the external monitor.

7. The food intake restriction system of claim 4, wherein the pressure sensing system includes a variable capacitance capacitor, the capacitance of the capacitor varying in response to pressure changes in the working fluid, the variation in the capacitance providing a measurement of the working fluid pressure.

8. The food intake restriction system of claim 4, wherein the working fluid is transferable between the port and the restriction device in a closed fluid circuit to affect the size of the gastro-intestinal restriction.

9. The food intake restriction system of claim 4, wherein the pressure sensing system measures the working fluid pressure and transmits the pressure measurement data to the external monitor during an adjustment of the food intake restriction device.

10. The food intake restriction system of claim 4, wherein the pressure sensing system includes a variable inductance coil adjacent the deformable surface, the inductance of the coil varying in response to pressure changes in the working fluid, the variation in inductance providing a measurement of the working fluid pressure.

* * * * *